(12) United States Patent
Hastie et al.

(10) Patent No.: US 11,511,101 B2
(45) Date of Patent: *Nov. 29, 2022

(54) LOADING GUIDE LUMEN

(71) Applicant: ABIOMED, Inc., Danvers, MA (US)

(72) Inventors: Caitlyn Hastie, Billerica, MA (US);
Frank Kirchhoff, Uebach-Palenberg (DE); Thorsten Siess, Wuerselen (DE)

(73) Assignee: ABIOMED, INC., Danvers, MA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/830,999

(22) Filed: Mar. 26, 2020

(65) Prior Publication Data

US 2020/0222608 A1 Jul. 16, 2020

Related U.S. Application Data

(63) Continuation of application No. 15/666,689, filed on Aug. 2, 2017, now Pat. No. 10,617,808, which is a
(Continued)

(51) Int. Cl.
*A61M 60/148* (2021.01)
*A61M 1/00* (2006.01)
(Continued)

(52) U.S. Cl.
CPC ............ *A61M 60/148* (2021.01); *A61M 1/00* (2013.01); *A61M 25/0108* (2013.01);
(Continued)

(58) Field of Classification Search
None
See application file for complete search history.

(56) References Cited

U.S. PATENT DOCUMENTS 7,022,100 B1 4/2006 Aboul-Hosn et al.
7,736,296 B2 6/2010 Siess et al.
(Continued)

FOREIGN PATENT DOCUMENTS

DE 10059714 C1 5/2002
EP 1207934 A2 5/2002
(Continued)

OTHER PUBLICATIONS

EP Search Report from EP 17 15 1268 dated Jun. 2, 2017.
(Continued)

*Primary Examiner* — Michael W Kahelin
(74) *Attorney, Agent, or Firm* — Botos Churchill IP Law LLP (57) ABSTRACT

An apparatus is disclosed including: an intracardiac pump device having a path for a guidewire extending through the pump device from a first opening to a second opening; and a lumen which extends from a first end located outside of the pump device, into the pump device through the first opening in the pump device, along the path for the guidewire, out of the pump device through the second opening, and to a second end located outside of the pump device. The lumen is configured to receive the guidewire such that when the guidewire passes through the lumen from the first end to the second end, the guidewire is positioned along the path.

9 Claims, 7 Drawing Sheets

Related U.S. Application Data continuation of application No. 15/206,573, filed on Jul. 11, 2016, now Pat. No. 9,750,861, which is a continuation of application No. 14/468,119, filed on Aug. 25, 2014, now Pat. No. 9,402,942, which is a continuation of application No. 13/552,366, filed on Jul. 18, 2012, now Pat. No. 8,814,776, which is a continuation of application No. 13/309,184, filed on Dec. 1, 2011, now abandoned.

(60) Provisional application No. 61/418,735, filed on Dec. 1, 2010.

(51) Int. Cl.

| | | |
|---|---|---|
| *A61M 25/01* | (2006.01) | |
| *A61M 60/13* | (2021.01) | |
| *A61M 60/405* | (2021.01) | |
| *A61M 60/865* | (2021.01) | |
| *A61M 60/237* | (2021.01) | |
| *A61M 60/867* | (2021.01) | |
| *A61M 25/09* | (2006.01) | |
| *A61M 25/00* | (2006.01) | |
| *A61M 60/414* | (2021.01) | |

(52) U.S. Cl.
CPC ............ *A61M 25/09* (2013.01); *A61M 60/13* (2021.01); *A61M 60/237* (2021.01); *A61M 60/405* (2021.01); *A61M 60/865* (2021.01); *A61M 60/867* (2021.01); *A61M 25/0009* (2013.01); *A61M 60/414* (2021.01); *A61M 2210/125* (2013.01)

(56) References Cited

U.S. PATENT DOCUMENTS

| | | |
|---|---|---|
| 8,814,776 B2 | 8/2014 | Hastie et al. |
| 8,888,728 B2 | 11/2014 | Aboul-Hosn et al. |
| 9,327,068 B2 | 5/2016 | Aboul-Hosn et al. |
| 9,402,942 B2 | 8/2016 | Hastie et al. |
| 2005/0154250 A1 | 7/2005 | Aboul-Hosn et al. |
| 2008/0076959 A1 | 3/2008 | Farnan et al. |
| 2009/0182188 A1* | 7/2009 | Marseille .......... A61M 25/0662 600/16 |
| 2016/0317730 A1 | 11/2016 | Hastie et al. |

FOREIGN PATENT DOCUMENTS

| | | |
|---|---|---|
| JP | 4159781 B2 | 10/2008 |
| WO | 9958170 A1 | 11/1999 |
| WO | 2007112033 A2 | 10/2007 |
| WO | 2008034068 A2 | 3/2008 |

OTHER PUBLICATIONS

International Preliminary Report on Patentability for PCT Appl. Ser. No. PCT/US2011/062851 dated Jun. 3, 2013 (10 pages).
International Search Report from PCT/US2011/062851 dated Feb. 28, 2012 (6 pages).

* cited by examiner

LOADING GUIDE LUMEN

CROSS-REFERENCE TO RELATED APPLICATIONS

The present application is a continuation of U.S. patent application Ser. No. 15/666,689 filed Aug. 2, 2017, now U.S. Pat. No. 10,617,808, which claims a priority benefit, under 35 U.S.C. § 120, as a continuation application of U.S. patent application of Ser. No 15/206,573, filed Jul. 11, 2016, now U.S. Pat. No. 9,750,861, which is a continuation of U.S. patent application Ser. No. 14/468,119, filed Aug. 25, 2014, now U.S. Pat. 9,402,942, which is a continuation of U.S. patent application Ser. No. 13/552,366, filed Jul. 18, 2012, now U.S. Pat. No. 8,814,776, which is a continuation of U.S. patent application Ser. No. 13/309,184, filed Dec. 1, 2011 (abandoned), which claims benefit of U.S. Provisional Application No. 61/418,735, filed Dec. 1, 2010. The entire contents of the foregoing applications are hereby incorporated by reference.

BACKGROUND

An intracardiac blood pump is a blood pump that is at least partially introduced into the heart to deliver blood from the heart into an artery, wherein the pump may protrude through a surgical opening in the heart. Typical intracardiac blood pumps have a maximum outer diameter of about 10-15 mm. A special form of intracardiac blood pumps are intravascular blood pumps. They are introduced into the heart through the vascular system of the patient, the incision site being spaced from the heart. Typically, intracardiac blood pumps inserted (e.g., percutaneously) into a patient's body are highly miniaturized, with a maximum outer diameter of 8 mm or less. In many cases, the introduction of an intravascular pump device involves the use of a guidewire to position the device.

Examples of intracardiac and intravascular blood pumps may be found in the following references, the entire contents of each of which is incorporated by reference herein: International Publication WO/2005/016416, published Apr. 20, 2006, International Publication WO/2005/016416, published Feb. 24, 2005; International Publication WO/2002/043791, published Jun. 6, 2002; International Publication WO/2002/015963, published Feb. 28, 2002; International Publication WO/2001/039817, published Jun. 7, 2001; and International Publication WO/1999/058170 published Nov. 18, 1999.

Further examples include the family of blood pumps available from Abiomed, Inc. of Danvers, Mass. under the Impella brand, including the Impella 2.5 pump, the Impella 5.0 pump, and the Impella LD.

SUMMARY

Medical devices, such as intracardiac blood pumps may be introduced into a patient (e.g., percutaneously) using a guide wire. In some cases, the device is loaded onto the guidewire by passing the guidewire through the device. Typically, the guidewire must follow a selected guidewire path through the device, in order to avoid damaging the device, and to ensure proper operation of the guidewire. The applicants have realized that the techniques described herein may be used to provide a guidewire loading lumen which can be used to improve the ease and reliability of loading the device onto the guidewire. The lumen extends through the device along a desired guidewire path. A guidewire may then be threaded through the lumen by a practitioner performing the introduction operating, ensuring that the guidewire is properly positioned through the device. The lumen may then be removed prior to introduction of the device into the patient.

In one aspect an apparatus is disclosed including: an intracardiac pump device having a path for a guidewire extending through the pump device from a first opening to a second opening; and a lumen which extends from a first end located outside of the pump device, into the pump device through the first opening in the pump device, along the path for the guidewire, out of the pump device through the second opening, and to a second end located outside of the pump device. In some embodiments, the lumen is configured to receive the guidewire such that when the guidewire passes through the lumen from the first end to the second end, the guidewire is positioned along the path.

In some embodiments, the lumen is configured such that, after the guidewire is received by the lumen and positioned along the path for the guidewire, the lumen may be removed without disturbing the guidewire from the path.

Some embodiments include a label attached to the second end of the lumen, where the label includes instructions for placing the guidewire along the path using the lumen.

In some embodiments, at least a portion of the lumen has a color which differs from the color of the pump device.

In some embodiments, the lumen is configured to allow the guide wire to be positioned through the device along the path without substantially flexing the guidewire.

In some embodiments, the pump device includes: a proximal drive portion including a motor; a distal pump portion connected to a distal end of the drive portion; one or more discharge ports positioned between the drive portion and the pump portion; an inflow cannula connected to the distal end of the pump portion, the cannula having a distal end including an inflow opening; and a flexible tubular pigtail extension connected to the distal end of the inflow cannula. In some embodiments, the guidewire path runs through the tubular pigtail extension, from the pigtail extension into the inflow cannula, through the inflow cannula into the pump portion, and out through a selected one of the one or more discharge ports. In some embodiments, the lumen extends from a first end located outside of the pump device, into the pump device through the first opening in the pigtail extension, along the path for the guidewire, out of the pump device through the second opening including the selected one of the one or more discharge ports, and to a second end located outside of the pump device.

In some embodiments, the second end of the lumen extends at least about 0.1 cm, 0.5 cm, 1.0 cm, 2.0 cm, 5.0 cm or more (e.g. in the range of 0.1-10 cm or any subrange thereof) outside of the selected one of the one or more discharge ports.

In some embodiments, first end of the lumen extends at least about 1.0 mm, about 2.0 mm, about 3.0 mm, about 4.0 mm, about 5.0 mm or more (e.g. in the range of 1-10 mm or any subrange thereof) outside of the first opening in the pigtail extension.

In another aspect, a method is disclosed including: obtaining a lumen; and inserting the lumen into an intracardiac pump device having a path for a guidewire extending through the pump device from a first opening to a second opening. In some embodiments, inserting the lumen includes positioning the lumen such that the lumen extends from a first end located outside of the pump device, into the pump device through the first opening in the pump device, along the path for the guidewire, out of the pump device through the second opening, and to a second end located outside of the pump device. In some embodiments, the lumen is configured to receive the guidewire such that when the guidewire passes through the lumen from the first end to the second end, the guidewire is positioned along the path.

In some embodiments, the lumen is configured such that, after the guidewire is received by the lumen and positioned along the path for the guidewire, the lumen may be removed without disturbing the guidewire from the path.

Some embodiments include attaching a label to the second end of the lumen, where the label includes instructions for placing the guidewire along the path using the lumen.

In some embodiments, at least a portion of the lumen has a color which differs from the color of the pump device.

In some embodiments, the lumen is configured to allow the guide wire to be positioned through the device along the path without substantially flexing the guidewire.

In some embodiments, the pump device includes: a proximal drive portion including a motor; a distal pump portion connected to a distal end of the drive portion; one or more discharge ports positioned between the drive portion and the pump portion; an inflow cannula connected to the distal end of the pump portion, the cannula having a distal end including an inflow opening; and a flexible tubular pigtail extension connected to the distal end of the inflow cannula. In some embodiments, the guidewire path runs through the tubular pigtail extension, from the pigtail extension into the inflow cannula, through the inflow cannula into the pump portion, and out through a selected one of the one or more discharge ports. In some embodiments, positioning the lumen includes positioning the lumen such that the lumen extends from a first end located outside of the pump device, into the pump device through the first opening in the pigtail extension, along the path for the guidewire, out of the pump device through the second opening including the selected one of the one or more discharge ports, and to a second end located outside of the pump device.

In some embodiments, positioning the lumen includes positioning the lumen such that the second end of the lumen extends at least about 0.1 cm, 0.5 cm, 1.0 cm, 2.0 cm, 5.0 cm or more (e.g. in the range of 0.1-10 cm or any subrange thereof) outside of the selected one of the one or more discharge ports.

In some embodiments, positioning the lumen includes positioning the lumen such that the first end of the lumen extends at least about 1 mm, about 2 mm, about 3 mm, about 4 mm, about 5 mm or more (e.g. in the range of 1-10 mm or any subrange thereof) outside of the first opening in the pigtail extension.

In another aspect, a method of loading an intracardiac pump device onto a guidewire is disclosed including obtaining an apparatus including: the intracardiac pump device having a path for the guidewire extending through the pump device from a first opening to a second opening; and a lumen which extends from a first end located outside of the pump device, into the pump device through the first opening in the pump device, along the path for the guidewire, out of the pump device through the second opening, and to a second end located outside of the pump device. In some embodiments, the lumen is configured to receive the guidewire such that when the guidewire passes through the lumen from the first end to the second end, the guidewire is positioned along the path.

In some embodiments the method further includes inserting the guidewire through the lumen to position the guidewire along the path and removing the lumen while leaving the guidewire positioned along the path.

Some embodiments include, after removing the lumen, introducing the pump device into a subject using the guide wire.

Various embodiments may include any of the above described features, either alone, or in any suitable combination.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate one or more embodiments described herein and, together with the description, explain these embodiments. Like reference characters refer to the same parts throughout the different views. The drawings are not necessarily to scale, emphasis instead being placed upon illustrating the principles of the embodiments.

DETAILED DESCRIPTION

Figure 1:
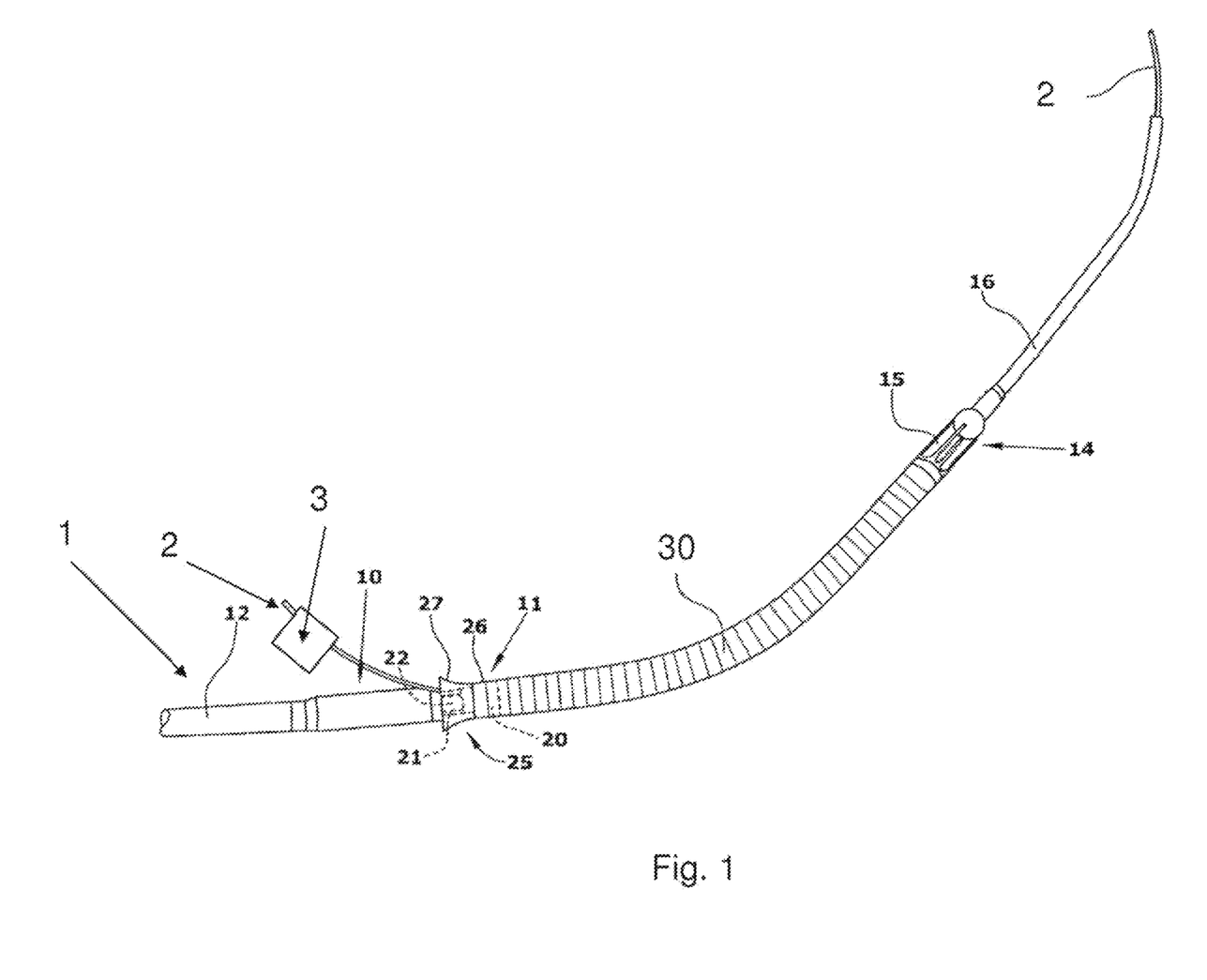
FIG. 1 is an illustration of an intracardiac pump device with a loading lumen.
Figure 5:
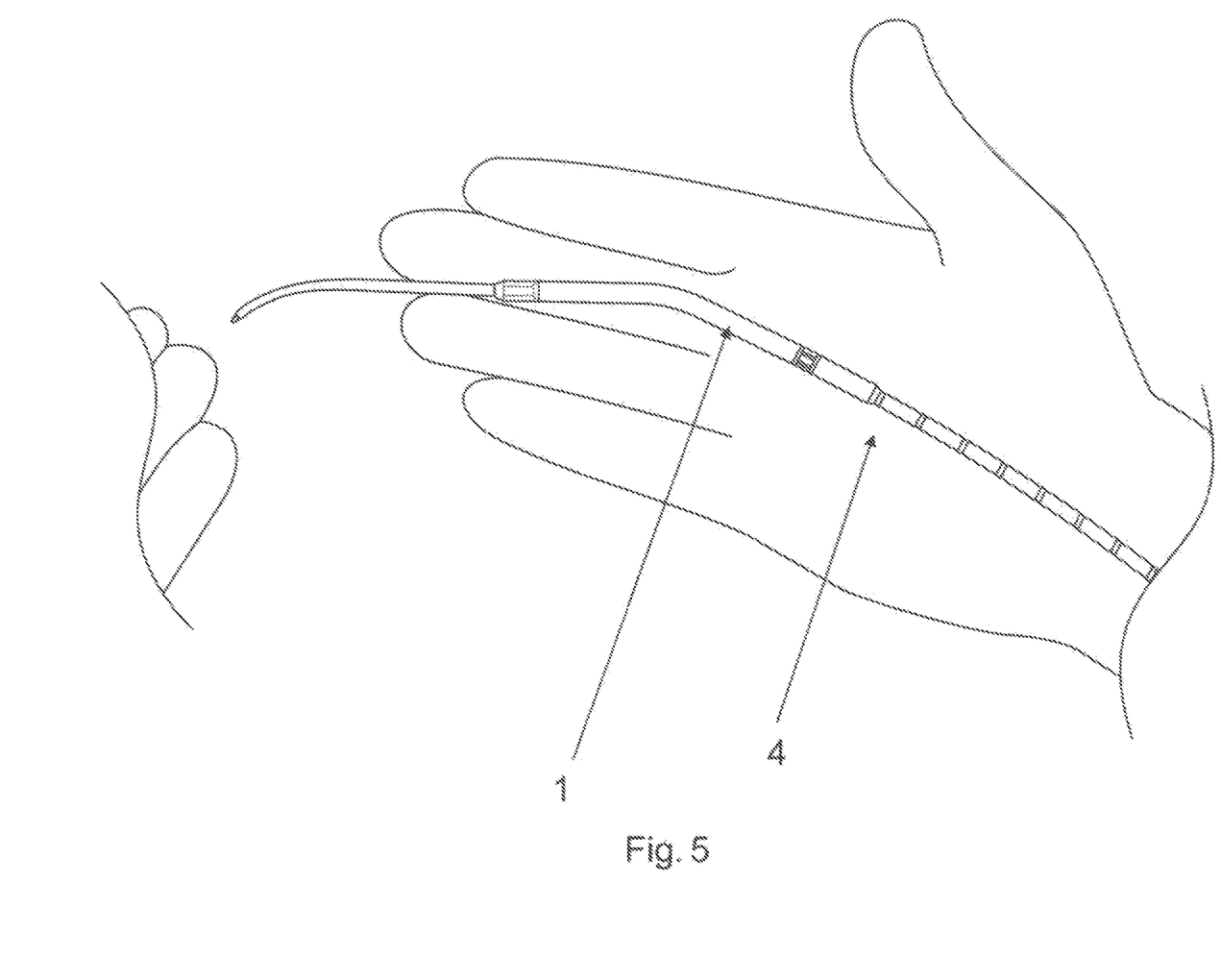
FIG. 5 is a photograph of an intracardiac pump loaded onto a guidewire.

Referring to FIG. 1, an intracardiac pump device 1 is provided that is intended for loading onto a guidewire 4 (e.g., as shown in FIG. 5 below). The pump device 1 includes a desired path for the guidewire extending through the pump device from a first opening to a second opening. A lumen 2 extends from a first end located outside of the pump device 1, into the pump device 1 through the first opening in the pump device 1, along the path for the guidewire 4, out of the pump device 1 through the second opening, and terminates at a second end located outside of the pump device 1. In some embodiments, the lumen 2 receives the guidewire 4 such that when the guidewire passes through the lumen from the first end to the second end, the guidewire is positioned along the path.

As detailed below, in some embodiments, the lumen 2 operates such that, after the guidewire is received by the lumen and positioned along the path for the guidewire, the lumen may be removed without disturbing the guidewire from the path (e.g., resulting in a properly loaded device 1 on the guidewire 4, as shown in FIG. 5 below).

In some embodiments, the lumen 2 allows the guide wire 4 to be positioned through the device 1 along the desired guidewire path without substantially flexing the guidewire 4, and also protects the device 1 from damage during loading onto the guidewire 4.

In various embodiments, the device 1 may include any suitable intracardiac pump device. As shown, the intracardiac pump device 1 includes a drive portion 10 and a pump portion 11 coaxial thereto. The drive portion 10 includes a motor (not illustrated). The proximal end of the drive portion 10 is connected with a catheter 12 holding the electric lines for operating and controlling the blood pump. The pump portion 11 is connected with a cannula 30 in the form of an elongate flexible hose whose distal end is provided with a suction head 14 having inflow openings 15. Contiguous to the suction head 14 is a soft elastic extension 16 that mechanically, yet not hydraulically extends the cannula 30. This extension 16 is provided with a pigtail tip to allow for atraumatic support on body tissue (as shown the pigtail tip is uncurled). The extension 16 is a hollow tubular member.

The pump portion 11 has a pump ring 20 that is connected with the drive portion 10 through longitudinally extending webs 21. Between the webs 21, the discharge ports 22 are situated through which blood exits radially to then flow along the outer side of the drive portion 10.

Optionally, in some embodiments, a screen 25 is provided at the pump portion 11. It includes an annular sleeve 26 sitting on the pump ring 20 and a continuously flaring guide portion 27 projecting proximally from the pump ring. The beginning of the guide portion 27 is at the upstream end of the discharge ports 22, i.e. at the end adjoining the pump ring 20.

In some embodiments, the outer diameter of the drive portion 10 and of the pump portion 11 is 4.0 mm. The outer diameter of the optional screen 25 is 5.6 to 6.0 mm. The wall thickness of the screen is 0.1 to 0.2 mm. The screen is made of a flexible material, for example of polyurethane. It may be formed integral with the cannula 30.

As shown, the lumen 2 has been inserted into the device 1. The lumen extends from a first end through the extension 16, through the cannula 30, through the pump portion 11, and out of one of the discharge ports 22 to terminate in a second end outside of the pump device 1. As shown, the pump device 1 is curved, and the lumen 2 extends out through a discharge port 22 located on the inner circumference of the pump device 1. The path of the lumen 2 corresponds to the desired guidewire path through the device 1.

In various embodiments, the lumen 2 may be made of any suitable material, e.g., a plastic or polymer material. In one embodiment, the lumen 2 is made of polyurethane (PU). The lumen 2 can be any suitable size and shape. In one embodiment (appropriate for use with the Impella 2.5 pump available from Abiomed, Inc. of Danvers, Mass.), the lumen 2 is a tubular polyurethane lumen with an inner diameter of 0.55 mm and an outer diameter of 0.75 mm. A lumen of this size fits through the pump device 1 along the desired guidewire path, and is able to receive a guidewire with a diameter of up to 0.4 mm (corresponding to an 0.018 inch guidewire, commonly available in the art).

In some embodiments, at least a portion of the lumen has a color which differs from the color of the pump device and/or the color of the guide wire. For example, the lumen 2 may have a bright red exterior, making the lumen clearly visible to a user, and providing a visual reminder to remove the lumen 2 prior to introducing the device into the patient.

Figure 2:
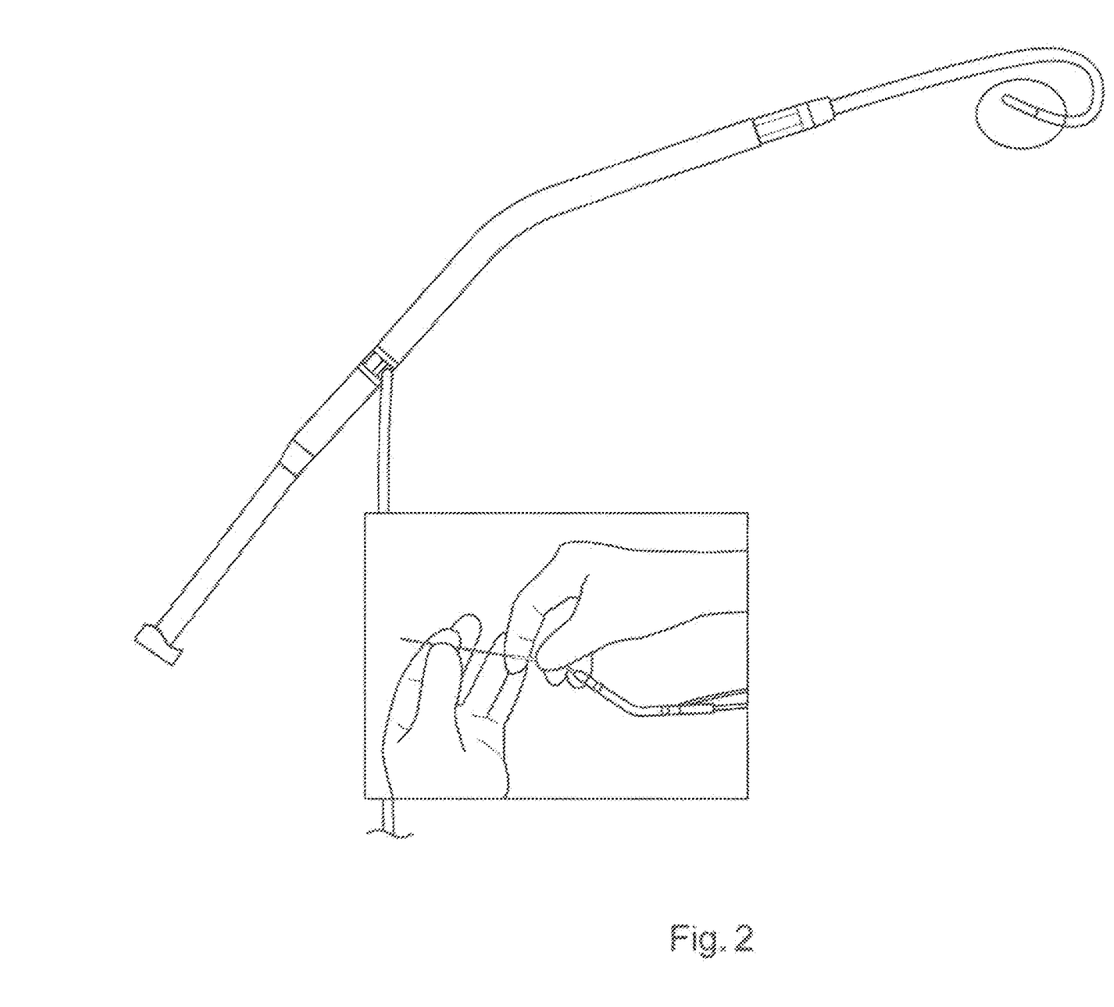
FIG. 2 is a photograph of an pump device with a loading lumen.

In various embodiments, the ends of the lumen 2 may extend any suitable distance outside of the pump device 1. For example, FIG. 2 shows a photograph of an embodiment featuring the lumen 2 in a pump device 1, where the pump device is an Impella 2.5 pump available from Abiomed, Inc. of Danvers, Mass. As shown, a first end of the lumen 2 extends in the range of 4-5 mm from the pigtail extension of the pump device 1. A second end of the lumen 2 extends about 1 cm from a discharge port of the pump device 1.

In some embodiments, first end of the lumen extends at least about 1 mm, about 2 mm, about 3 mm, about 4 mm, about 5 mm or more (e.g. in the range of 1-10 mm or any subrange thereof) from the pigtail extension of the device.

In some embodiments, positioning the second end of the lumen extends at least about 0.1 cm, 0.5 cm, 1.0 cm, 2.0 cm, 5.0 cm or more (e.g. in the range of 0.1-10 cm or any subrange thereof) from the discharge port.

As shown in FIGS. 1 and 2, in some embodiments, a label 3 is attached to the lumen 2. The label may include printed or other visual information, including instruction for loading the pump device 1 onto the guidewire 4 using the lumen 2. In some embodiments, the size of the label may be chosen to prevent insertion into the patient (e.g., the size may be chosen larger than the typical incision size used in a percutaneous introduction procedure). This will help ensure that the pump device 1 is not mistakenly inserted prior to removal of the lumen 2. In some embodiments, the label 3 may be made of a fluid resistant material (e.g. a plastic), and may be attached to the lumen 2 in any suitable fashion (e.g., using an adhesive). In some embodiments the label 3 may be formed integral with the lumen 2.

Figure 3:
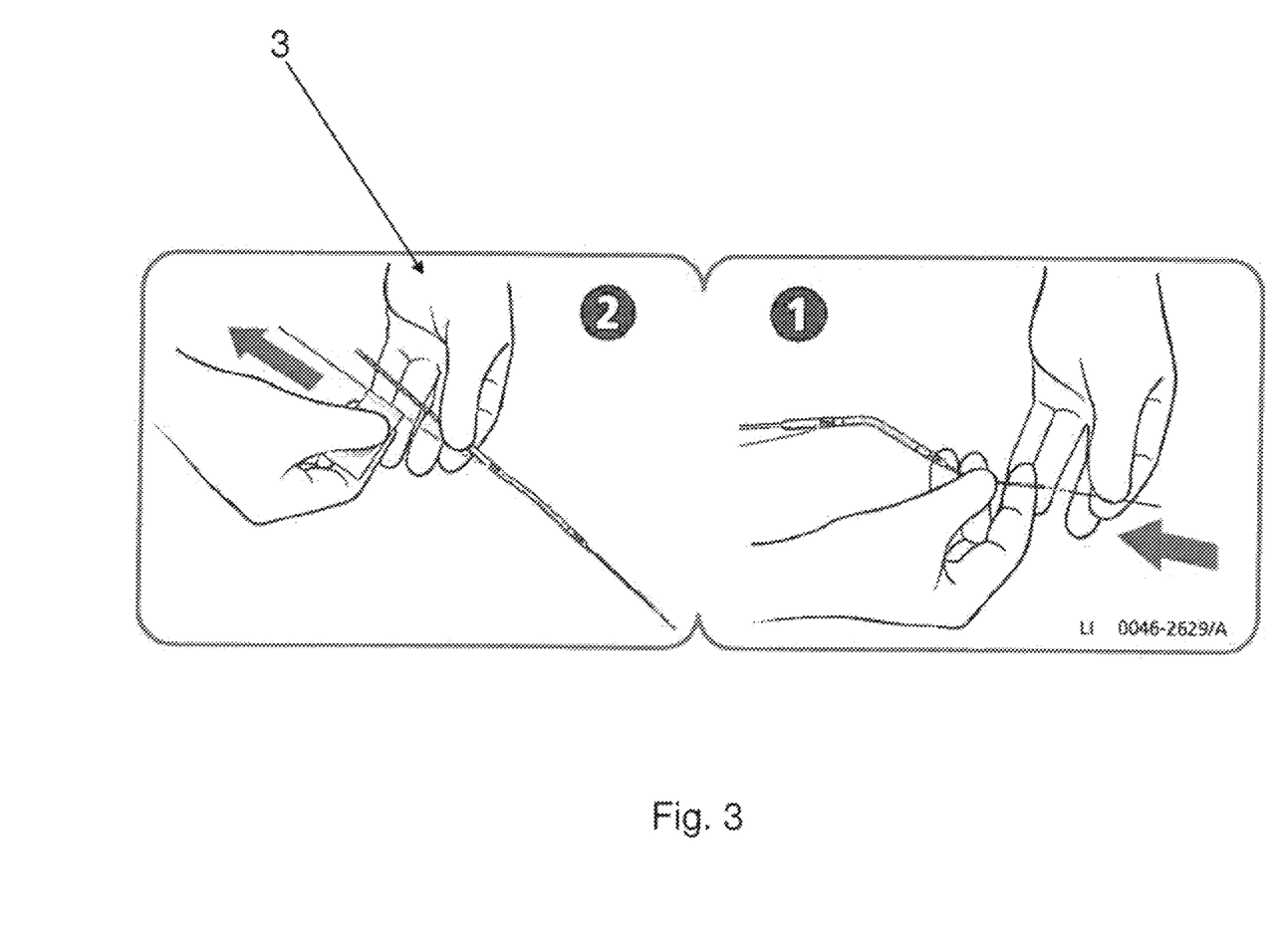
FIG. 3 is an illustration showing an instruction label for a loading lumen.

FIG. 3 shows an exemplary embodiment of the label 3. As shown the label 3 has instruction graphics printed on a front side (shown), and an adhesive on a back side (not shown). The label 3, can be folded around the lumen 3 and caused to adhere to itself, to provide a two sided flag-like element with visual information appearing on both sides of the flag.

Figure 4A:
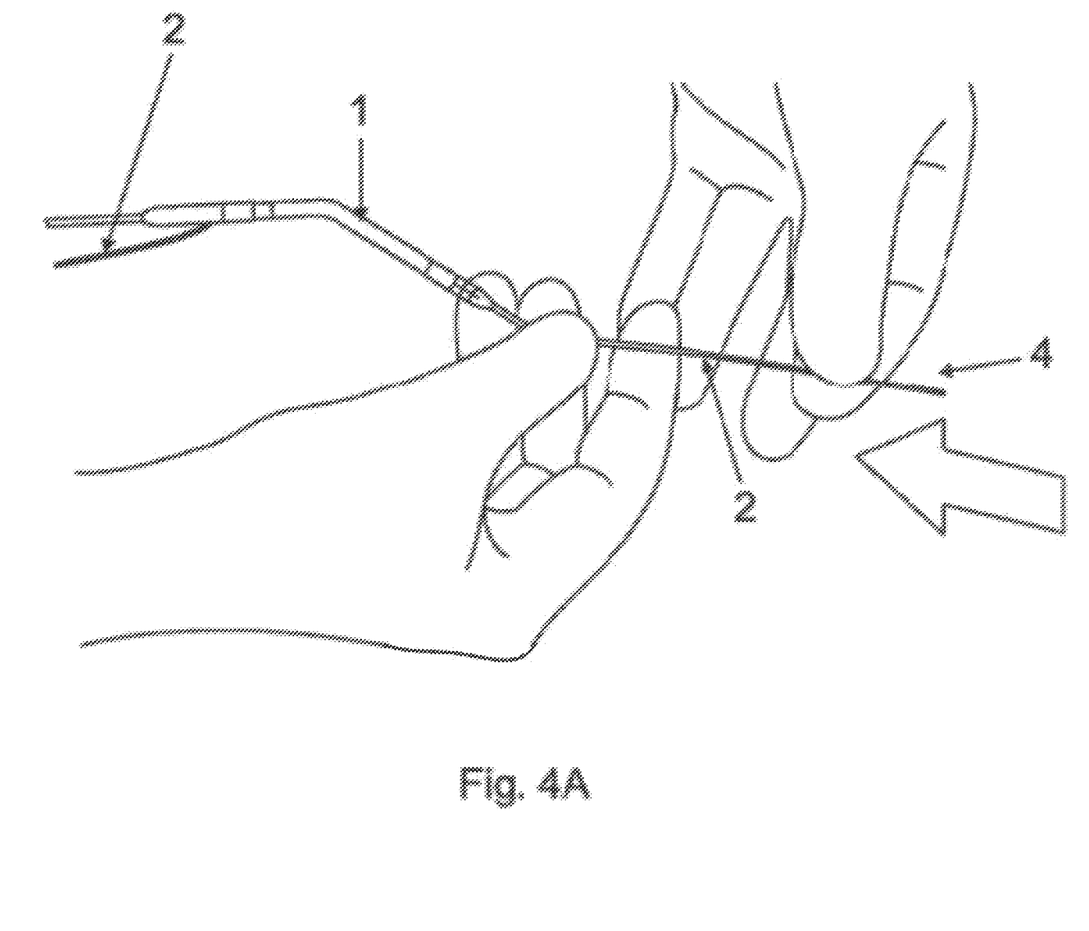
FIG. 4A is an illustration showing the insertion of a guidewire into a loading lumen in an intracardiac pump device.
Figure 4B:
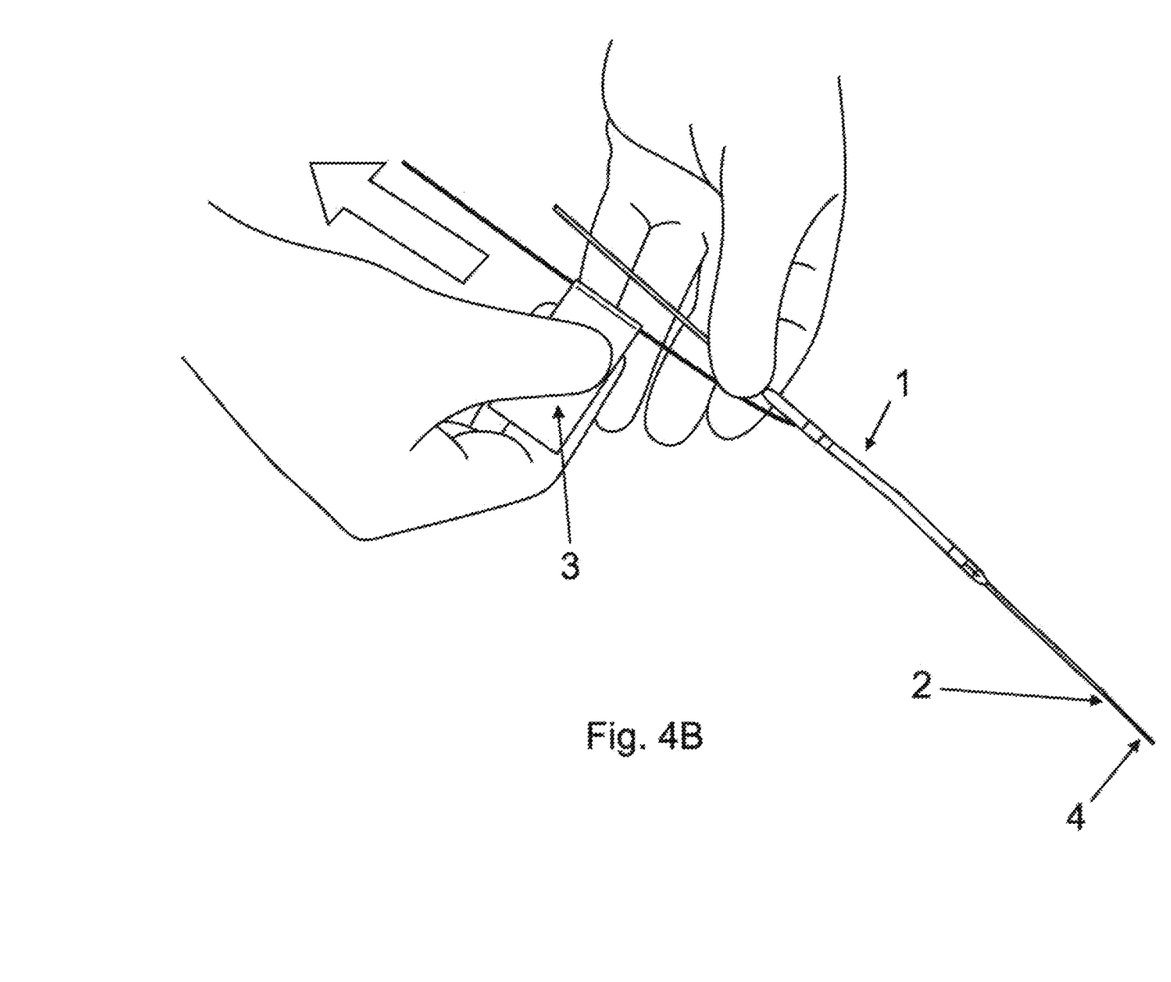
FIG. 4B is an illustration showing removal of a loading lumen from an intracardiac pump following the insertion of a guidewire into the loading lumen.

FIGS. 4A and 4B illustrate the loading of the pump device 1 onto the guidewire 4 using the lumen 2. As shown in FIG. 4A, the pigtail extension of the pump device 1 is uncurled. An end of the guidewire 4 is inserted into the end of the lumen 2 extending from the pigtail. The guidewire 4 is advanced through the lumen 2 until the end of the guidewire exits the other end of the lumen 2 extending from the discharge port of the pump. Note that during insertion of the guidewire 4, the lumen 2 serves to prevent flexing of the guidewire, and protects the internal parts of the pump device.

As shown in FIG. 4B, once the end of the guidewire 4 has passed through the lumen 2, the lumen 2 may be removed, leaving the guidewire behind, positioned along the desired guidewire path. The lumen 2 is pulled over the guidewire towards the end extending from the discharge port until the lumen 2 completely exits the pump device 1 and comes clear off the guidewire 4. In some embodiments, the lumen 2 is then discarded.

In some embodiments, the pump device 1 may be shipped to an end user with the lumen 2 already installed. Accordingly, the positioning of the lumen 2 along the desired guidewire path may undergo quality control. The lumen 2 then acts as a guide for the end use during loading on the guidewire 4, resulting in reduced user error. For example, the use of the lumen 2 can reduce or eliminate errors related to passing the guidewire through an incorrect discharge port on the pump device 1.

FIG. 5 is a photograph of the pump device 1 loaded on the guidewire 4 after the lumen 2 has been completely removed. The pump device 1 can now be introduced into a patient using the guidewire, e.g., as described below with reference to FIG. 6.

Figure 6:
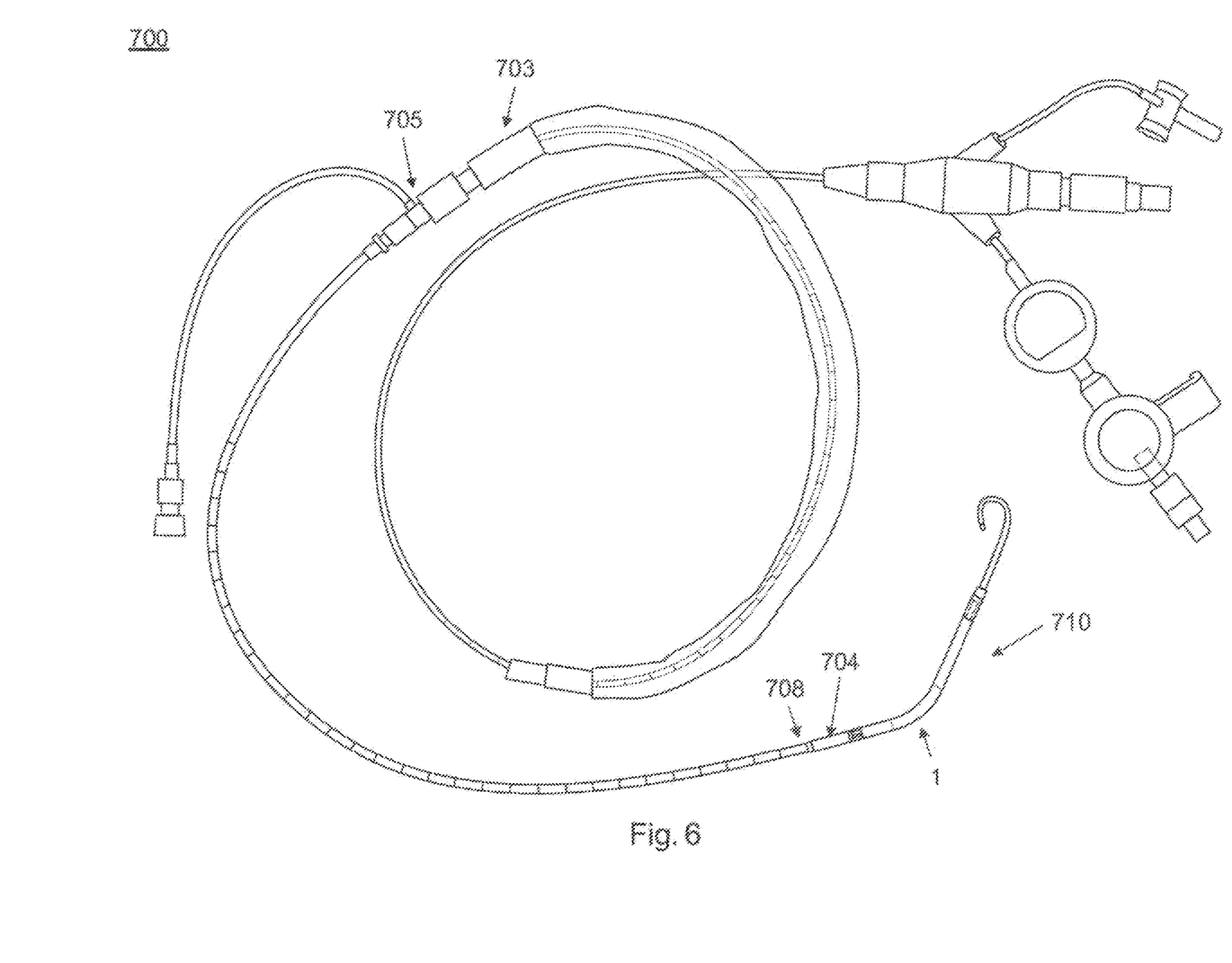
FIG. 6 is an illustration of an intracardiac blood pump system.

FIG. 6 shows a catheter system 700 with an intracardiac blood pump 1. The pump may be, for example the Impella 2.5 blood pump available from Abiomed Inc. of Danvers, Ma. The blood pump 1 is a catheter mounted microaxial flow pump capable of pumping up to, e.g., 2.5 L/min of blood from the left ventricle to the systemic circulation. Using a monorail type insertion platform, the blood pump 1 is placed via a femoral arterial sheath 703 (e.g., a 13 Fr sheath). The cannula portion 710 of the device which, during use, sits across the aortic valve is contiguous to and integrated motor 704 that comprises the largest diameter section of the catheter (e.g., at 12 Fr). A repositioning device 705 allows removal of the sheath 703 after placement, leaving the modest (e.g. 9F) catheter in the arterial system. The pump 1 is powered and controlled by a control console (not shown), e.g., an Impella series control panel available from Abiomed Inc. of Danvers, Ma. An arterial infusion pump (not shown) controls a purge system designed to keep the corrosive plasma from entering the motor compartment of the pump 1.

The pump 1 is inserted via a modified monorail technique under direct fluoroscopic control. Pressure monitoring using a pressure lumen 708 adjacent to the motor as well as motor current monitoring are used to give positioning verification to the operator. The device is placed using fluoroscopic control to avoid kinking the catheter and compromising the purge lumen. After arterial access is obtained, the 13 F peel-away sheath is positioned. A coronary guiding catheter (e.g., a JR-4 catheter) and subsequently a 0.018" wire is placed across the aortic valve into the left ventricle. Once the 0.018" wire is across the aortic valve, the guiding catheter is removed and the pump catheter is threaded onto the 0.018" wire, e.g., using the loading lumen 2 (not shown) as described in detail above. With the device positioned in the ventricle, the wire is removed and the pump 1 activated at minimum level, just enough to counteract the regurgitation coming down the cannula from the proximal aorta into the ventricle now that the cannula is placed across the aortic valve.

Once the pump 1 is positioned across the aortic valve, the control panel can be utilized to confirm that the device placement is proper and stable. At this point, the device performance level is typically adjusted to a higher performance level.

Further details regarding the use of the system 700 may be found in D. H. Raess and D. M. Weber, J. of Cariovasc. Trans. Res. (2009) 2:168-172.

Although a number of examples have been given above related to guidewire loading lumens used with intracardiac blood pumps, it is to be understood that the techniques applied herein may be used for other applications, including the guidewire loading of any other suitable types of medical devices intended for use on human or animal subjects.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "including" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "or" as defined above. For example, when separating items in a list, "or" or "or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

In the claims, as well as in the specification above, all transitional phrases such as "including," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All definitions, as defined and used herein, should be understood to control over dictionary definitions, definitions in documents incorporated by reference, and/or ordinary meanings of the defined terms.

Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. An intracardiac pump device comprising:
   a drive portion and a pump portion, the pump portion having a path for a guidewire extending through the pump portion from a first opening interposed between the drive portion and the pump portion to a second opening in operative connection with the pump portion wherein the drive portion is coaxial with the pump portion;
   a catheter, wherein the catheter is coupled to a proximal end of the drive portion; and
   a lumen positioned in the pump portion, the lumen extending from a first end of the lumen located outside of the pump portion into the pump portion through the first opening in the pump portion, along the path for the guidewire, and out of the pump portion through the second opening in the pump portion to a second end located outside of the pump portion,
   wherein the lumen is configured to receive the guidewire such that when the guidewire passes through the lumen from the first end of the lumen to the second end of the lumen, the guidewire is positioned along the path.

2. The intracardiac pump device according to claim 1, wherein the lumen is removably positioned in the intracardiac pump device, such that, after the guidewire is received by the lumen and positioned along the path for the guidewire, the lumen may be removed from the pump portion without disturbing the guidewire from the path through the pump portion.

3. The intracardiac pump device according to claim 1 further comprising a cannula, wherein the second opening in the pump portion is a discharge port of the pump portion and wherein the discharge port is coupled to the cannula.

4. The intracardiac pump device according to claim 1, wherein the drive portion is a proximal drive portion and the pump portion is a distal pump portion, wherein the proximal drive portion comprises a motor.

5. The intracardiac pump device according to claim 1, wherein the first opening is a discharge port.

6. The intracardiac pump device according to claim 1, wherein the lumen has a first color, the lumen has a second color and the intracardiac pump device has a third color, wherein the first, second and third colors are different from each other.

7. The intracardiac pump device according to claim 3, wherein a proximal end of the cannula is coupled to the discharge port of the pump portion and a distal end of the cannula comprises a suction port.

8. The intracardiac pump device according to claim 7, further comprising a flexible tubular pigtail extension connected to the distal end of the cannula.

9. The intracardiac pump device according to claim 8, wherein the path for the guidewire runs through the flexible tubular pigtail extension, from the flexible tubular pigtail extension into the suction port of the cannula, through the cannula into the pump portion, and out through the first opening.

* * * * *